United States Patent [19]

Burbaum et al.

[11] Patent Number: 5,908,776
[45] Date of Patent: Jun. 1, 1999

[54] CELL CULTURE CHAMBER FOR MULTIPLE WELL PLATES

[75] Inventors: Jonathan J. Burbaum, Cranbury; Stephen Skwish, Hamilton, both of N.J.

[73] Assignee: Pharmacopeia, Inc., Cranbury, N.J.

[21] Appl. No.: 09/055,850

[22] Filed: Apr. 6, 1998

[51] Int. Cl.[6] .................................................. C12M 3/00
[52] U.S. Cl. ............................. 435/288.3; 435/288.4; 435/305.3; 435/305.4; 422/102
[58] Field of Search ................ 435/288.3, 288.4, 435/305.1, 305.2, 305.3, 305.4, 307.1; 422/102

[56] References Cited

U.S. PATENT DOCUMENTS 5,587,321 12/1996 Smith et al. ........................ 435/305.3
5,700,655 12/1997 Croteau ................................. 435/30

*Primary Examiner*—David A. Redding

[57] ABSTRACT

Cell culture chambers and incubators are operated to grow cells under a wide variety of conditions. Where those conditions result in too rapid evaporation of the well media for low volume wells such as those found in 1536-well plates, a subchamber is provided to increase the local humidity so that media evaporation is controlled to an acceptable level. A local liquid source is provided. That liquid may be water or an isotonic solution matched to the well media for a particular application.

17 Claims, 4 Drawing Sheets

CELL CULTURE CHAMBER FOR MULTIPLE WELL PLATES

FIELD OF THE INVENTION

The present invention relates generally to improvements in cell culture chambers and more particularly to advantageous methods and apparatus for the use of such chambers in conjunction with multiple well plates having a large plurality of small wells of low volume, such as the presently used 1536-well plates.

BACKGROUND OF THE INVENTION

Many screening assays, both for the detection of potential therapeutics and for the isolation of clonal populations, require cells to be cultured in microtiter plates. The small well size and volume of the 1536-well plate make conventional methods of culturing cells inadequate under certain conditions. Under those conditions, evaporation of media is too rapid to support cell growth.

While the volumes of typical sample plates having larger well volumes than those found in 96-well plates is such that standard approaches may be employed without too rapid evaporation of media to support cell growth, once the volume of individual wells begins to get below 10 μl, evaporation of the media from the wells begins to be a problem. At the 1 μl well volume typical of the 1536-well plate described in U.S. Provisional Patent Application Ser. No. 60/037,636 filed Feb. 18, 1997 and incorporated by reference herein, too rapid evaporation of well media can be a substantial problem.

This problem cannot necessarily be solved by simply increasing the humidity of the cell culture chamber. For example, at a temperature of 37° C., it may be impossible to increase the chamber humidity above approximately 95% humidity. This limitation results because the sides of the chamber are typically sufficiently cooler than the chamber air temperature that condensation occurs and water comes out of the chamber atmosphere as quickly as it is added. As a consequence, at this temperature and maximum global humidity, too rapid evaporation of well media may still occur.

It will be recognized to be highly advantageous to provide a simple, cost effective solution to this and other problems which result when multiple well plates having low volume wells such as 1536-well plates are utilized in standard cell culture chambers.

SUMMARY OF THE PRESENT INVENTION

The present invention recognizes that while it may not be a simple matter to increase the global humidity of a cell culture chamber, it may be possible to raise the local humidity and thereby address the rapid evaporation problem. To this end, the present invention provides methods and apparatus to sufficiently increase the local humidity in the vicinity of the low volume wells of a multi-well plate to address this problem while maintaining the conditions necessary for cell growth, such as, ambient temperature and gas exchange. A variety of subchambers are described herein which may utilize water or an isotonic solution as desired to suit the applications at hand.

A more complete understanding of the present invention, as well as further features and advantages of the invention, will be apparent from the following Detailed Description and the accompany drawings.

DETAILED DESCRIPTION

Figure 1A:
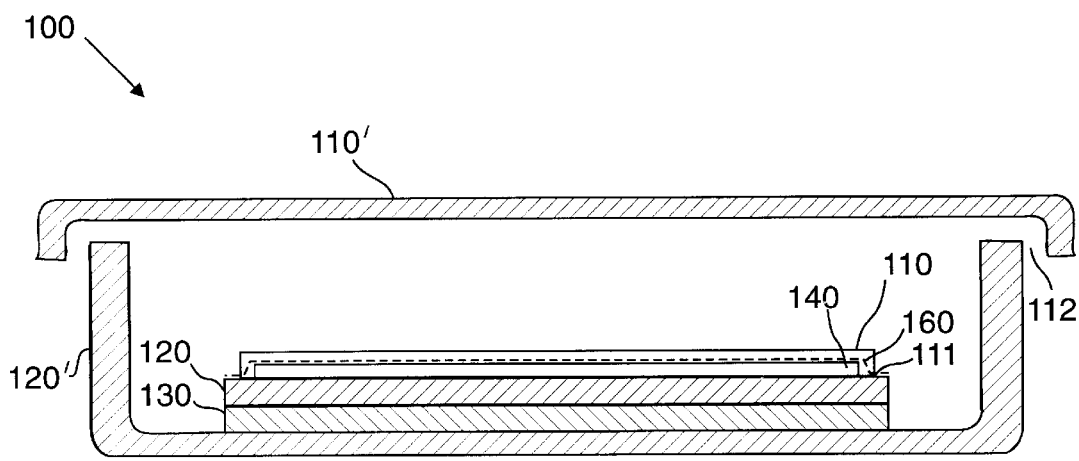
FIG. 1A is a side view illustrating a first embodiment of the present invention which may suitably be employed to reduce media evaporation while maintaining the conditions necessary for cell growth.

FIG. 1A illustrates various aspects of a subchamber 100 in accordance with the present invention which may be utilized to address the too rapid evaporation problem while maintaining the conditions necessary for cell growth. The subchamber 100 is defined by a plate cover 110 which may suitably be made from glass or a plastic which is appropriate for use with the temperature and other environmental conditions to be employed, and two sheets of wet blotter paper 120 and 130. The plate cover will preferably be rectangular in shape and have an area slightly larger than a standard 1536-well plate 140. For a 1536-well plate having the approximate dimensions 4⅞"×3³⁄₁₆"×³⁄₃₂", a plate cover having the approximate dimensions 5"×3½"×¼" has been found suitable. Thus, the volume above the wells in subchamber 100 is substantially smaller than the volume of a cell chamber or an incubator, such as chamber 150 shown in FIG. 1B. For other size plates, the dimensions of cover 110 maybe adjusted accordingly.

An edge 111 of the plate cover rests on the top sheet of wet blotter paper 120. The bottom sheet of wet blotter paper 130 sits on a bottom surface of a base 120'. A top piece 110' covers base 120'. A gap 112 between top piece 110' and base 120' allows for gas exchange between the atmosphere of a cell chamber or incubator and the wells of the plate 140 as discussed further below in conjunction with FIG. 1B.

Figure 1B:
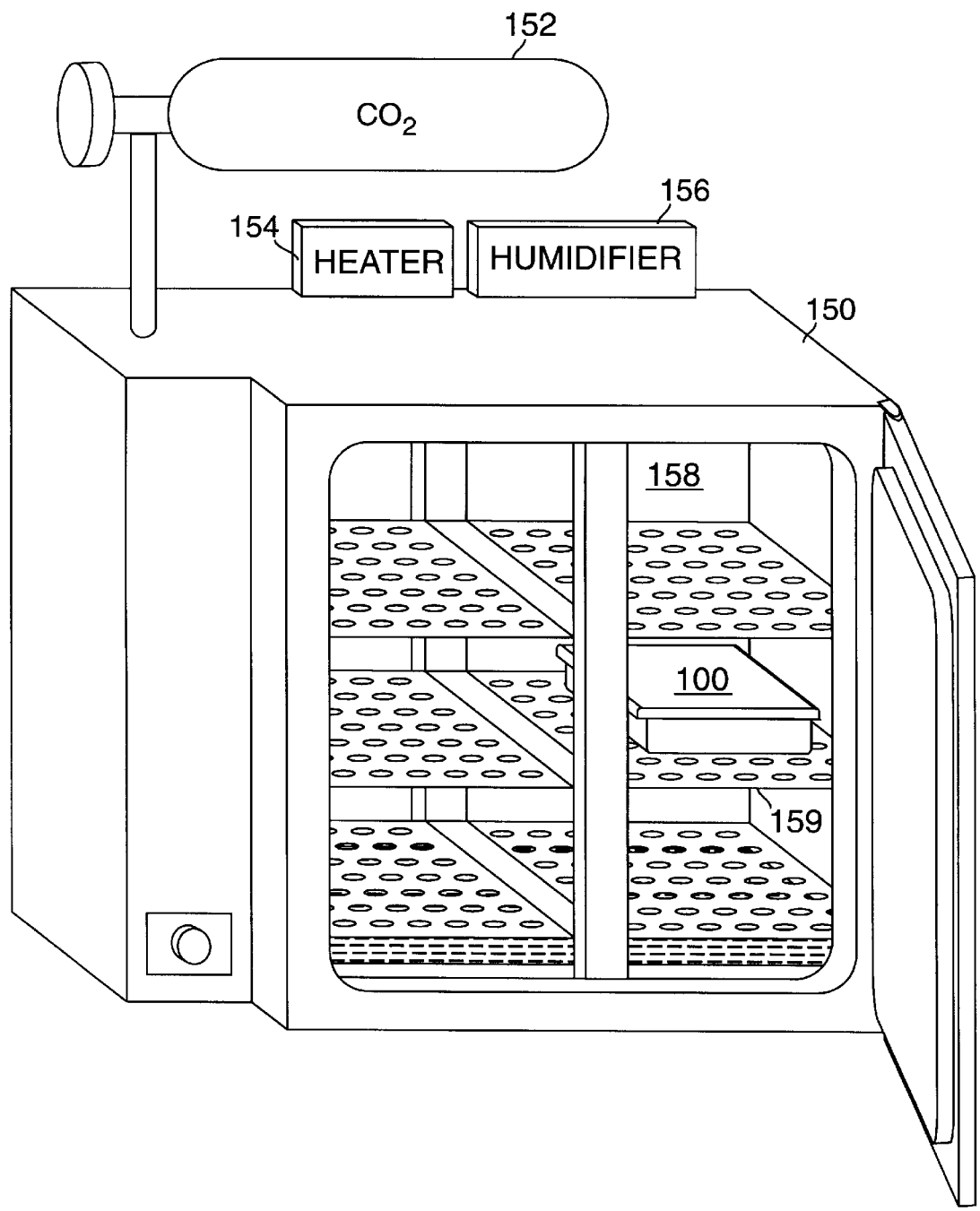
FIG. 1B illustrates a cell culture chamber with the subchamber of FIG. 1 placed therein.

As shown in FIG. 1B, a cell chamber or tissue incubator 150 includes an adjustable source 152 of carbon dioxide, $CO_2$, for maintaining a desired level of $CO_2$ in the atmosphere of the chamber 150, an adjustable heater 154 for maintaining the desired temperature in the chamber, and an adjustable humidifier 156 for adjusting the humidity in the chamber. It will be recognized that the cell chamber 150 and its components are shown representationally and not drawn to scale, and that the present invention may be adapted for use with any cell chamber, incubator or the like in which it is desired to adjust conditions locally with respect to multi-well plates (rather than attempting and possibly failing to do so globally).

The subchamber 100 is shown on a rack 159 of cell chamber 150. It will be recognized that subchambers 200 and 300 also can be placed therein. In operation, the wet blotter sheets 120 and 130 of subchamber 100 may suitably be Whatman 3MM cellulose filter paper. They allow gas from the atmosphere 158 inside chamber 150 to pass to the smaller volume beneath the plate cover 110. The blotter sheets 120 and 130 may be wet with water or an isotonic solution matching or better matching the solutions in the wells of 1536-well plate 140. For example, a common tissue culture medium, such as Dulbecco's Modified Eagle Media (D-MEM), high glucose with L-glutamine, Penicillin Streptomycin liquid, qualified Fetal Bovine Serum, Gluta MAX-II Supplement, Hygromycin B, or the like, has many dissolved solutes that can change the equilibrium between vapor and liquid phase water. If pure water were used to saturate the filter paper pad, then the tissue culture medium would absorb water from the atmosphere and the volume of the wells would increase. However, if the same medium (or a solution with comparable evaporation characteristics) were used instead of pure water, the equilibria (from filter to vapor and from well to vapor) would be identical, and no volume change would occur. Evaporation of the liquid within the blotter sheets 120 and 130 will dominate evaporation to the chamber 150 from the wells of the 1536-well plate thereby increasing the local humidity under plate cover 110 in the vicinity of the wells of the 1536-well plate. These phenomena reduce the rate of evaporation from those wells to an acceptable level. Optionally, a semi-permeable membrane 160, shown in dashed lines in FIG. 1A, such as Gore Tex™ may be placed over the wells of 1536-well plate 140. This option may also be employed in the other embodiments described above.

Figure 2:
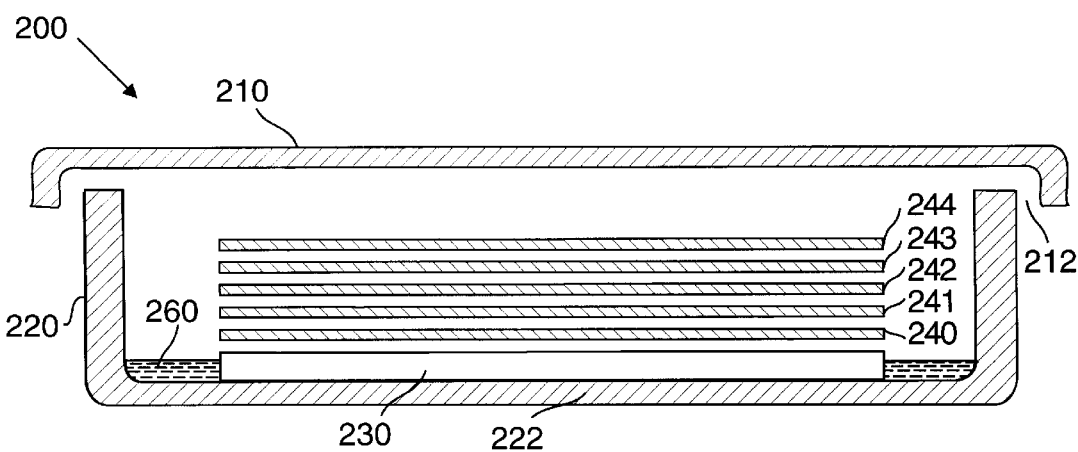
FIG. 2 is a side view of a second embodiment of the present invention comprising a subchamber for use within a cell culture chamber or incubator to increase local humidity in the vicinity of the wells of several multi-well plates.

A second embodiment of the present invention is shown in FIG. 2. In this embodiment, a subchamber 200 is designed for use with multiple culture plates to be maintained within limited incubator space at the same time. Subchamber 200 includes a top piece 210 and a base 220. A spacer member 230 is centrally located on a bottom surface 222 of the base 220. Five 1536-well plates 240, 241, 242, 243 and 244 are spaceably stacked on the spacer 222. A series of additional spacers (not shown) may be employed to space the 1536-well plates 240–244. Alternatively, the base 220 may have molded supports rising above the base so that the edges of 1536-well plates slide into the supports like an oven rack or a drawer slides into its support. A host of other supporting arrangements may also suitably be employed.

A water or isotonic solution 260 is also contained in the bottom of the base 220. The level of liquid 260 is preferably below the top of the spacer 230. As was the case for the subchamber 100, the subchamber 200 is placed within a cell culture chamber, incubator or the like, such as the chamber 150, so that cells can be grown under controlled conditions in the wells of the plates 240–244. A gap 212 between top piece 210 and base 220 allows for gas exchange between the atmosphere of the cell culture chamber or incubator and the wells of the plates 240–244. Evaporation of the liquid 260 raises the local humidity within the subchamber 200 reducing the evaporation from the wells 240–244 to an acceptable level.

Figure 3A:
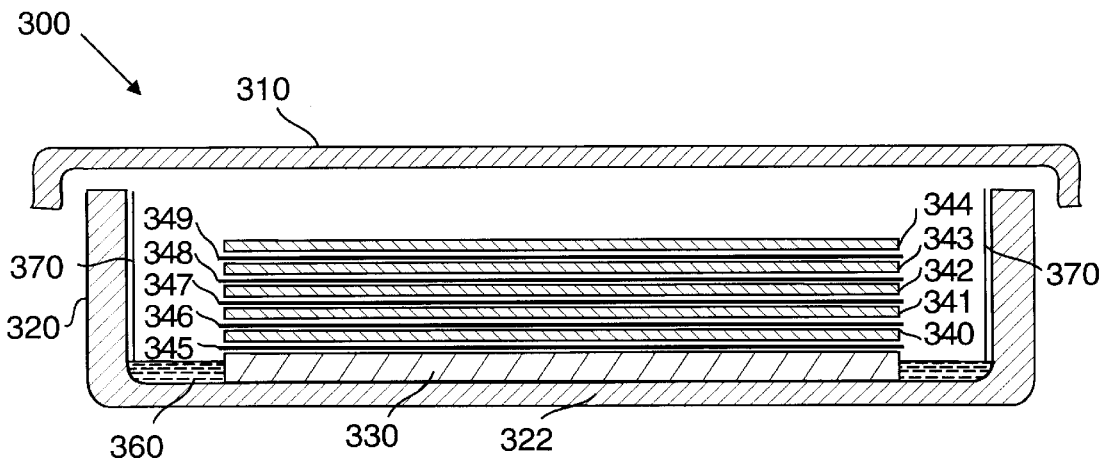
FIGS. 3A and 3B are side and top views, respectively, illustrating aspects of a third embodiment of the present invention comprising a subchamber for multiple plates within limited space.
Figure 3B:
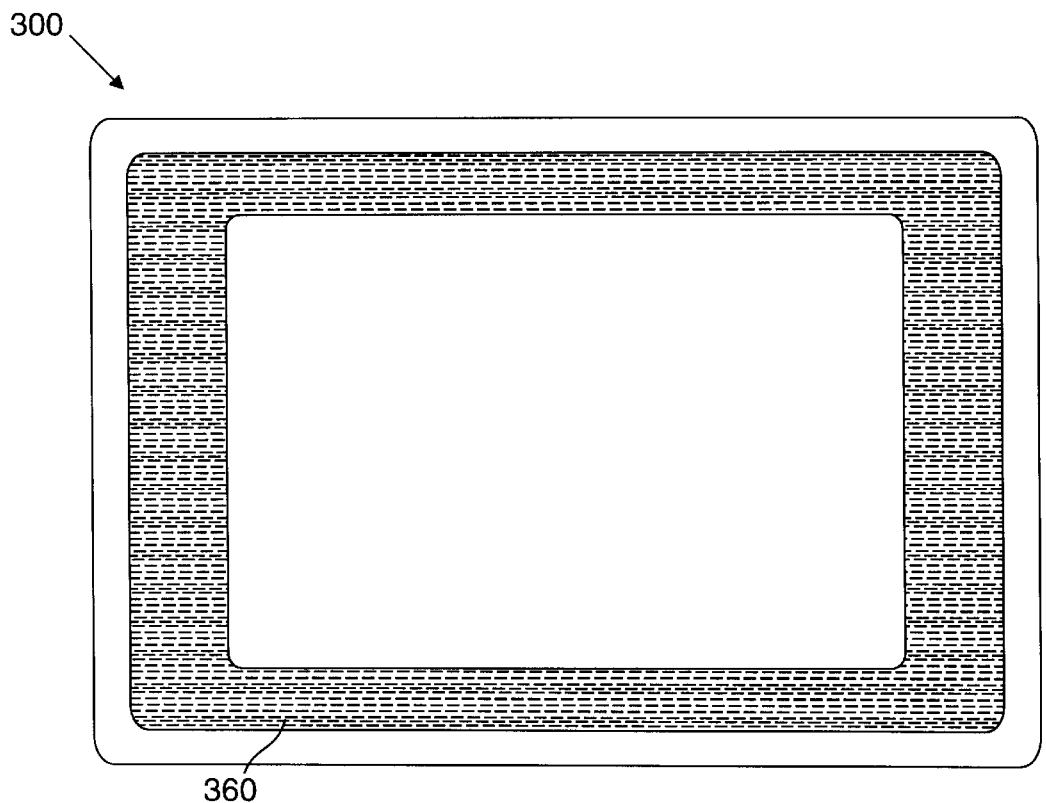

FIGS. 3A and 3B illustrate details of a third subchamber 300 in accordance with the present invention. Like subchamber 200, subchamber 300 includes a loose fitting lid 310 for gas exchange, a base portion 320 which supports a spacer member 330 surrounded by water or isotonic solution 360 as best seen in FIG. 3B. Five 1536-well plates 340–344 are stacked on the spacer member 330. The plates 340–344 are separated from one another by a series of spacers 345–349. Finally, filter paper 370 is also included. the filter paper 370 extends down into the liquid 360 and serves to wick that liquid up to the level of the plates 340–344 to help insure more uniform evaporation of the liquid 360 and more uniform conditions for all the wells in all of the plates 340–344.

Figure 4:
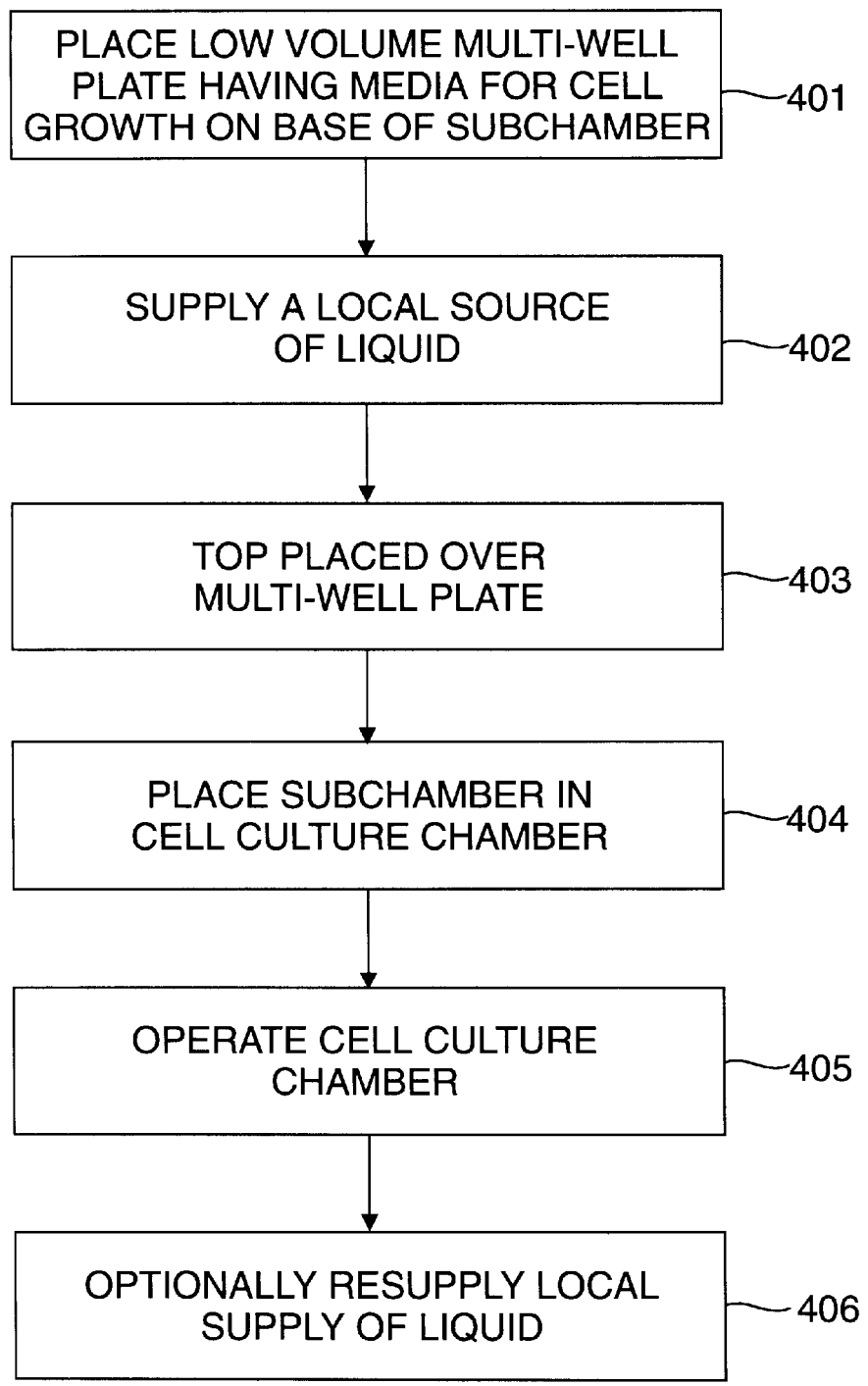
FIG. 4 illustrates a method in accordance with the present invention.

FIG. 4 illustrates a method 400 for utilizing multiple well plates having low volume wells under conditions in which rapid evaporation of well media could otherwise occur. The method 400 is adapted for use with wells of a size of 10 $\mu$l or less and is particularly advantageous for well sizes of 1 $\mu$l or less. In step 401, a low volume multi-well plate, such as a 1536-well plate, having media for cell growth is placed on the base of a subchamber, such as any of the subchambers 100, 200, or 300. A local source of liquid, such as water or isotonic solution, is supplied in step 402. For example, liquid may be provided in the sheets 120 and 130 or liquid 260 or 360 may be added to the subchambers 200 or 300.

In step 403, a top is placed over the multi-well plate to form a subchamber. This top, like the tops or plate covers 110, 210 or 310 allows gas exchange between the multi-well plate and a culture chamber once the subchamber is placed in the culture chamber and the chamber is operative to create the desired cell growth conditions.

In step 404, the subchamber is placed in a culture chamber. In step 405, the culture chamber is operated to create the desired cell growth conditions. Finally, in step 406, the local source of liquid may optionally be resupplied. For example, the cell chamber may be modified to include a detector to detect when the level of liquid reaches a predetermined low level and a liquid source which can then automatically supplement that supply.

While the present invention has been disclosed in its presently preferred context, it will be recognized that the present teachings may be employed in a variety of contexts. By way of example, while particularly well suited to use with 1536-well plates, the present invention will also be applicable to 96-well plates. Similarly, while applicable to cell growth in a culture chamber, it will also be applicable to other environments where such environmental control is desired. It is anticipated that, if plates with even higher numbers of wells having even smaller volumes should come into general use, that the present invention will be even more important for work with such plates.

We claim:

1. A subchamber used in combination with a multi-well plate having low volume wells containing media to be subjected to evaporative conditions to help control the rate of evaporation of said media, the subchamber comprising:
    a base supporting the multi-well plate and for containing a local source of liquid in a reservoir, the local source of liquid being in addition to any liquid in the low volume wells containing media to be subjected to evaporative conditions; and
    a top for covering the multi-well plate while permitting gas exchange between the wells of the multi-well plate and the atmosphere outside the subchamber.

2. The subchamber of claim 1 further comprising a sheet of semi-permeable membrane placed over the wells of the multi-well plate.

3. The subchamber of claim 1 wherein the wells have a volume of 10 $\mu$l or less.

4. The subchamber of claim 1 wherein the multi-well plate has at least 1536 wells.

5. The subchamber of claim 4 wherein each of the wells has a volume of approximately 1 $\mu$l or less.

6. A subchamber used in combination with a multi-well plate having low volume wells containing media to be subjected to evaporative conditions to help control the rate of evaporation of said media, the subchamber comprising:
    a base supporting the multi-well plate and for containing a local source of liquid, the base comprising two sheets of wet blotter paper; and
    a top for covering the multi-well plate while permitting gas exchange between the wells of the multi-well plate and the atmosphere outside the subchamber.

7. The subchamber of claim 6 wherein the two sheets of blotter paper are wet with water.

8. The subchamber of claim 6 wherein the two sheets of blotter paper are wet with an isotonic solution selected to match the media in the wells.

9. A subchamber used in combination with a multi-well plate having low volume wells containing media to be subjected to evaporative conditions to help control the rate of evaporation of said media, the subchamber comprising:

a base supporting the multi-well plate and for containing a local source of liquid, the base comprising a pan which collects a liquid reservoir in its bottom, and the multi-well plate being supported above the top of the liquid reservoir by a spacer member; and a top for covering the multi-well plate while permitting gas exchange between the wells of the multi-well plates and the atmosphere outside the subchamber.

10. The subchamber of claim 9 wherein additional multi-well plates are stacked above said first multi-well plate.

11. The subchamber of claim 10 wherein said additional multi-well plates are separated from one another and said first multi-well plate utilizing spacers.

12. The subchamber of claim 9 wherein a sheet of filter paper has a first end inserted in the liquid reservoir and a second end which rises above said liquid reservoir to approximately the height of the top of the multi-well plate.

13. A method for controlling media evaporation from low volume wells of a multi-well plate comprising the steps of:

placing the multi-well plate on a base of a subchamber;

supplying a local source of liquid; and placing a top over the multi-well plate which allows gas exchange between the wells of the multi-well plate and the atmosphere outside the subchamber.

14. The method of claim 13 further comprising the steps of:

placing the subchamber in a cell culture chamber; and operating the cell culture chamber.

15. The method of claim 14 further comprising the step of:

detecting when the level of the local source of liquid reaches a predetermined level.

16. The method of claim 15 further comprising the step of resupplying the local source of liquid.

17. The method of claim 13 further comprising the step of:

selecting a liquid which matches the media of the wells and utilizing that liquid as said local source liquid.

* * * * *